(12) United States Patent
Ahmed

(10) Patent No.: US 6,193,682 B1
(45) Date of Patent: *Feb. 27, 2001

(54) LOW PROFILE NEONATAL HYDROCEPHALUS DEVICE AND METHODS

(76) Inventor: Abdul Mateen Ahmed, 928 E. Juanita Ave., La Verne, CA (US) 91750

( * ) Notice: Subject to any disclaimer, the term of this patent is extended or adjusted under 35 U.S.C. 154(b) by 0 days.

This patent is subject to a terminal disclaimer.

(21) Appl. No.: 09/039,546

(22) Filed: Mar. 16, 1998

(51) Int. Cl.[7] .................................................. A61M 5/00
(52) U.S. Cl. .................. 604/9; 604/8; 604/198; 604/246
(58) Field of Search .................... 604/8–10, 30, 604/31, 93, 246, 247, 500, 126, 128, 129

(56) References Cited

U.S. PATENT DOCUMENTS

| | | |
|---|---|---|
| 3,288,142 | 11/1966 | Hakim . |
| 3,527,226 | 9/1970 | Hakim . |
| 3,601,128 | 8/1971 | Hakim . |
| 3,623,484 | 11/1971 | Schulte . |
| 3,654,932 | 4/1972 | Newkirk et al. . |
| 3,690,323 | 9/1972 | Wortman et al. . |
| 3,768,508 * | 10/1973 | Schulte et al. ........................ 137/522 |
| 3,827,439 | 8/1974 | Schulte et al. . |
| 4,103,689 | 8/1978 | Leighton . |
| 4,240,434 | 12/1980 | Newkirk . |
| 4,364,395 * | 12/1982 | Redmond et al. ...................... 604/10 |
| 4,464,168 | 8/1984 | Redmond . |
| 4,554,918 | 11/1985 | White . |
| 4,560,375 | 12/1985 | Schulte et al. . |
| 4,588,394 | 5/1986 | Schulte et al. . |
| 4,681,560 | 7/1987 | Schulte et al. . |
| 4,741,730 * | 5/1988 | Dormandy et al. ....................... 604/8 |
| 4,850,955 | 7/1989 | Newkirk . |
| 4,898,583 | 2/1990 | Borsanyi et al. . |
| 4,898,584 | 2/1990 | Borsanyi et al. . |
| 4,898,585 | 2/1990 | Borsanyi et al. . |
| 5,152,753 | 10/1992 | Laguette et al. . |
| 5,176,627 * | 1/1993 | Watson ..................................... 604/8 |
| 5,662,600 * | 9/1997 | Watson et al. ........................... 604/8 |
| 5,728,061 * | 3/1998 | Ahmed ..................................... 604/9 |

FOREIGN PATENT DOCUMENTS 0 117 050 * 8/1994 (EP) ........................................ 604/8

OTHER PUBLICATIONS

Cardiac/Peritoneal Catheters/Radionics, No Date.*
Burr Hole Valve/Radionics, Not dated.
ICP Tele–Sensor,/Radionics, Not dated.
Neonatal Shunt Valve,/Radionics, Not dated.
Ventricular Catheters/Radionics, Not dated.
Encyclopedia of Neuroscience vol. 1994.
Shunt Obstruction: A Preventable Complication, 1993.

* cited by examiner

*Primary Examiner*—Glenn K. Dawson
*Assistant Examiner*—Jennifer Maynard
(74) *Attorney, Agent, or Firm*—John J. Connors; Connors & Associates

(57) ABSTRACT

Disclosed is a medical device for draining fluid which includes a shell made of a flexible, resilient material. The shell has an aerofoil-like shape with opposed ends and an anterior cavity and a posterior cavity separated by a partition wall. An inlet tube has a first end in communication with the fluid and a second end in communication with anterior cavity and an outlet tube has a first end in communication the posterior cavity and a second end from which the fluid is drained. A one-way directional flow valve is housed within the posterior cavity and it has an inlet end connected to the partition wall which is in communication with the anterior cavity and an outlet end in communication with the posterior cavity.

15 Claims, 3 Drawing Sheets

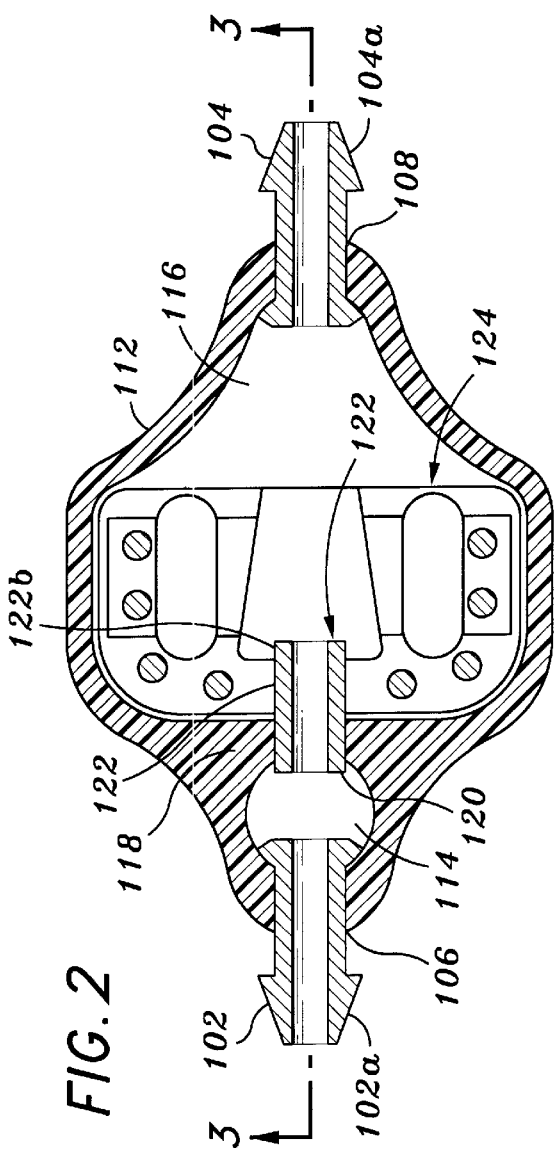
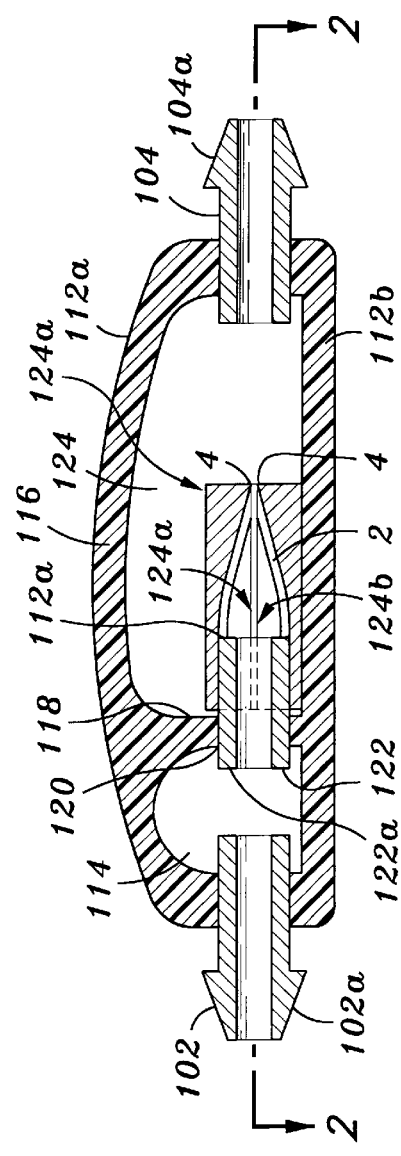
FIG. 2
FIG. 3

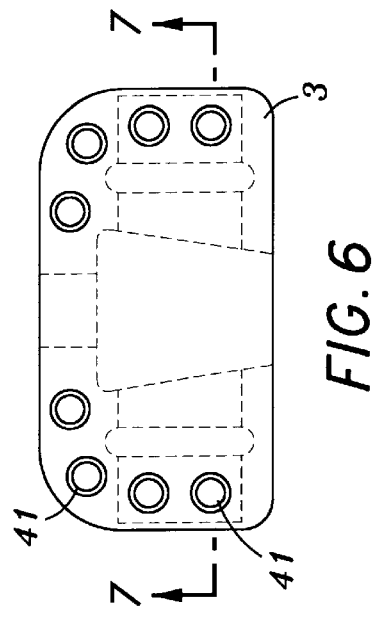
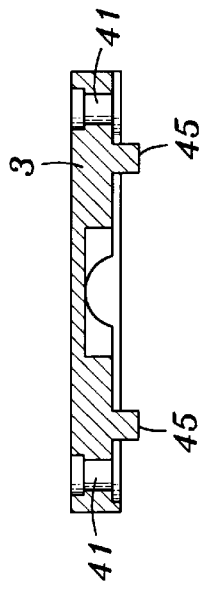
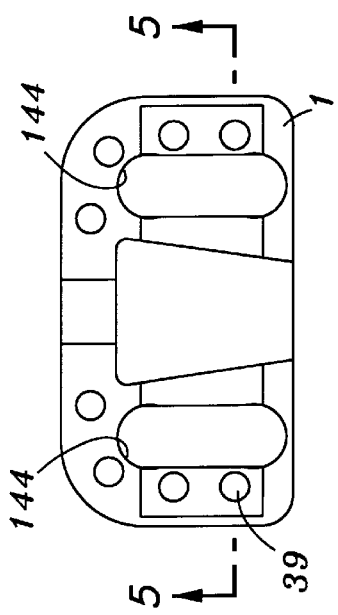
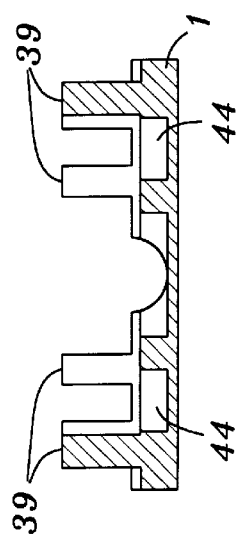
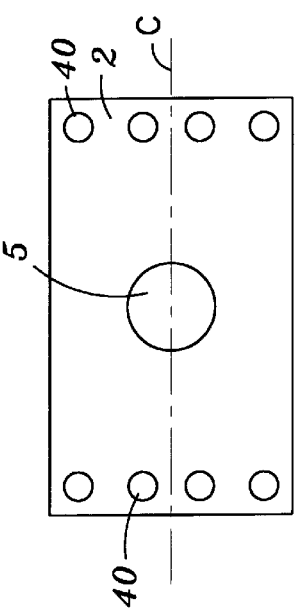

LOW PROFILE NEONATAL HYDROCEPHALUS DEVICE AND METHODS

BACKGROUND OF THE INVENTION

1. Field of Invention

This invention relates to medical devices which are implanted in the human body, and particularly, to a medical device used to treat hydrocephalus.

2. Background Discussion

"Hydrocephalus" is the diagnostic term meaning excess water in the brain or cranial vault due to the cerebral spinal fluid flow being blocked. When this occurs, the increased intracranial pressure causes the brain to flatten into a thin shell against the skull. In newborn babies this fluid pressure increase also causes the head to swell which, if left untreated, usually results in death. Hydrocephalus is discussed in greater depth in the "Encyclopedia of Neuroscience" Volume 1, Edited by George Adelman and published by Birkhauser. Medical valve type devices, sometimes referred to as shunts, are used to treat hydrocephalus. In an article entitled "Shunt Obstruction: A preventable Complication?" published in Pediatric Neurosurgery (1993, Volume 19, pages 156–164, C. Sainte-Rose discusses mechanical shunt complications.

As disclosed in U.S. Pat. No. 5,411,473, one type of valve (herein the Glaucoma Valve) has been used to treat glaucoma by allowing aqueous humor to flow from the intraocular chamber of the eye to relieve excess pressure. The Glaucoma Valve uses a membrane under tension to form its own fluid retention chamber. A slit-like opening is along adjoining, overlapping edges of portions of the membrane. The membrane responds to slight changes in fluid pressure and expands or contracts to open or close the opening. When opened, it provides a wide open mouth with parted lips that allows for free flow of fluid through it without any substantial resistance to fluid flow. This feature also substantially reduces the likelihood that the opening will be clogged by particulate matter. In a copending application of the inventor, U.S. Ser. No. 08/592,016, now U.S. Pat. No. 5,728,061, there is disclosed a device for treating individuals with hydrocephalus that uses the Glaucoma Valve. Although this device has several advantages over the prior art, it was not specifically designed for treating infants. The invention disclosed herein is an improvement over this device which is especially designed to be implanted in infants (children typically from about the age of 1 month to 4 years).

SUMMARY OF THE INVENTION

In accordance with this invention, the Glaucoma Valve has been enclosed within a uniquely shaped and sized flexible shell to provide a medical device that may be used to treat hydrocephalus in infants. This valve is especially suited for this application because its slit-like opening is not easily obstructed by particulates and it is self regulating, opening and closing in response to slight changes in pressure.

There are several features of this invention, no single one of which is solely responsible for its desirable attributes. Without limiting the scope of this invention as expressed by the claims, its more prominent features will now be discussed briefly. After considering this discussion, and particularly after reading the section of the application entitled "DETAILED DESCRIPTION OF THE PREFERRED EMBODIMENT," one will understand how the features of this invention provide its benefits, which include ease of implantation into a patient, especially small children, ease of manufacture, and reliability in draining fluid from a patient's body.

The first feature of the medical device of this invention is that it includes a shell having an aerofoil-like shape, and preferably having a maximum volume of about 0.275 cubic inch. The shell is made of a flexible, resilient material, preferably siliconized rubber, which is self sealing to allow the shell to be pierced with a needle that upon withdrawal leaves a puncture which is sealed due the resiliency of the material. Consequently, it is adapted to expand or contract in response to pressure. Preferably, the shell has a maximum height which is about 0.35 inch, a maximum width which is about 0.65 inch, and a maximum length which is about 1.2 inch. Typically, the height ranges between about 0.20 and about 0.35 inch, the width ranges between about 0.55 and about 0.85 inch, and the length ranges between about 0.8 and about 1.2 inch.

The second feature is that the shell includes an anterior cavity and a posterior cavity separated by a partition wall. The anterior cavity has a maximum volumetric capacity of about 0.030 cubic inch and the posterior cavity has a maximum volumetric capacity of about 0.110 cubic inch. Typically, the anterior cavity has a volumetric capacity ranging between about 0.018 and about 0.030 cubic inch and the posterior cavity has a volumetric capacity ranging between about 0.100 and about 0.150 cubic inch. The ratio of the volume of the anterior cavity to the volume of the posterior cavity ranges between about 1:4 to about 1:6.

The third feature is that the shell has opposed ends, one of which is tapered so that this tapered end is adapted for insertion into a patient's body. Preferably, both ends are tapered. There are a pair of tubes, one tube is an inlet tube in communication with one end and the other tube is an outlet tube in communication with the other end. The inlet tube has a first end in communication with the fluid in the patient's body (typically the cranium) to be drained and a second end in communication with the anterior cavity. The outlet tube has a first end in communicationt the posterior cavity and a second end from which the fluid is drained from the shell into the patient's stomach or heart.

The fourth feature is a one-way directional flow valve housed within the posterior cavity and connected to the partition wall. The one-way directional flow valve, preferably the Glaucoma Valve, has an inlet end which is in communication with the anterior cavity and an outlet end in communication with the posterior cavity. At a predetermined pressure, the valve allows fluid to flow through the inlet tube through the one-way directional flow valve and exiting the shell through the outlet tube. The one-way directional flow valve has a height ranging between about 0.100 and about 0.175 inch, a width ranging between about 0.60 and about 0.80 inch, and a length ranging between about 0.35 and about 0.65 inch. Preferably, the one-way directional flow valve has a pair of overlying membranes in tension which provide a chamber with a slit-like opening through which fluid exits the one-way directional flow valve into the posterior cavity. The chamber has a trapezoidal configuration with a minimum volumetric capacity of about 0.03 cubic inch to a maximum volumetric capacity of about 0.05 cubic inch. The overlying membranes are formed from a single sheet of siliconized rubber material having a thickness of at least about 0.0075 inch which is folded to form the slit-like opening, and a pair of plates maintain the membrane in tension. The folded sheet siliconized rubber material and the pair of plates have a substantially rectangular configuration.

The fifth feature is that the device is manufactured by insert molding where the inlet tube, the outlet tube, and the one-way directional flow valve are placed with a mold which is then filled with material to form the shell.

This invention also includes a method for treating hydrocephalus by draining the fluid from the cranial vault of a patient. The method includes (a) providing a medical device, including a shell including a pair of cavities, said shell having an aerofoil-like shape and a maximum height which is about 0.35 inch, a maximum width which is about 0.65 inch, and a maximum length which is about 1.2 inch, a pair of tubes, each tube having free ends and one tube in communication with one cavity and the other tube in communication with the other cavity, and a one-way directional flow valve housed within the one cavity that at a predetermined pressure allows fluid to flow through one tube into one cavity and then through the one-way directional flow valve into the other cavity and finally exiting the device through the other tube, (b) attaching the medical device to the patient, (c) inserting a free end of one tube into the cranial vault to enable fluid to drain through the free end of the one tube into the one cavity in the medical device, (d) inserting a free end of the other tube into the patient's body to enable fluid to drain from the other cavity into the body of the patient.

DESCRIPTION OF THE DRAWING

The preferred embodiments of this invention illustrating all of its features will now be discussed in detail. This embodiment depicts the novel and unobvious features of the medical device of this invention. The drawing accompanying this application, which is for illustrative purposes only, includes the following figures (FIG.), with like numerals indicating like parts:

FIG. 2 is a cross-sectional view with the valve membrane removed taken along line 2—2 of FIG. 3 (dimensions are shown in inches).

FIG. 3 is a cross-sectional view taken along line 3—3 of FIG. 2 (dimensions are shown in inches).

FIG. 4 is a plan view of the bottom plate of the valve enclosed in the hydrocephalus device of this invention (dimensions are shown in inches).

FIG. 5 is a cross-sectional view taken along line 5—5 of FIG. 4(dimensions are shown in inches).

FIG. 6 is a plan view of the top plate of the valve used in the hydrocephalus device of this invention(dimensions are shown in inches).

FIG. 7 is a cross-sectional view taken along line 7-7 of FIG. 6 (dimensions are shown in inches).

FIG. 8 is a plan view of the membrane used with the valve (dimensions are shown in inches).

DETAILED DESCRIPTION OF THE PREFERRED EMBODIMENT

Figure 1:
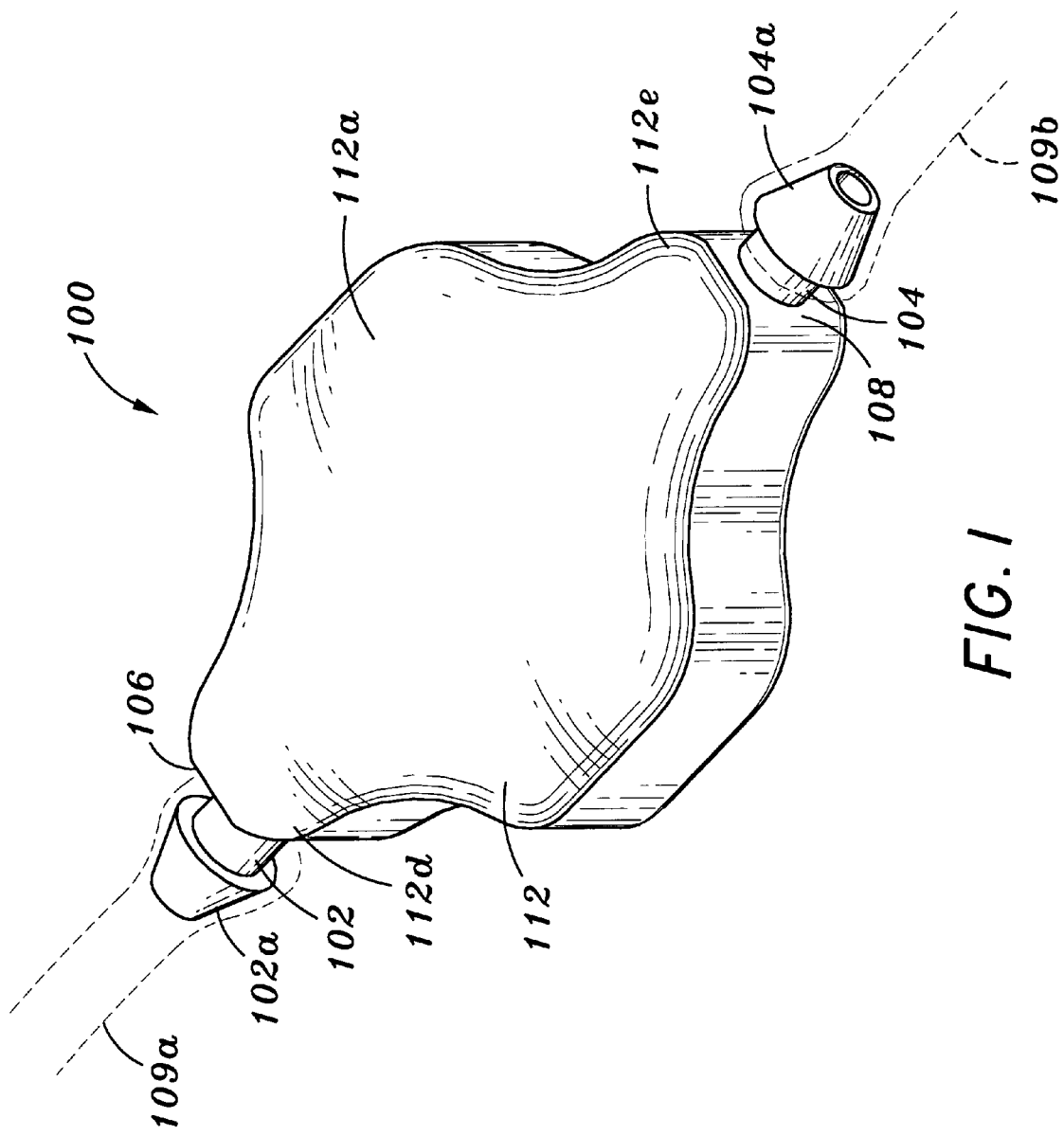
FIG. 1 is a perspective view of the hydrocephalus device of this invention.

As best shown in FIGS. 1, 2, and 3, the device 100 of this invention, which is especially suited for treating infants suffering from hydrocephalus, includes an especially shaped shell 112. The roof 112a of the shell 112 has a domed or curved shape and the floor 112b of the shell is substantially flat and planar. Consequently, the overall shape of the shell 112 is like an aerofoil. The shell 112 is integral, being molded from a flexible, resilient, bio-compatible material such as siliconized rubber, or PTFE (Teflon). This material is self sealing to allow the shell 112 to be pierced with a needle which upon withdrawal leaves a puncture which is sealed due the resiliency of the material.

The shell 112 has anterior cavity 112 and a posterior cavity 114 separated by a partition wall 118. The anterior cavity 114 has a maximum volumetric capacity of about 0.030 cubic inch, and the posterior cavity 116 has a maximum volumetric capacity of about 0.110 cubic inch. The posterior cavity 116 has a greater capacity than the anterior cavity, namely, that its volumetric capacity exceeds 0.30 cubic inch but is less than about 0.110 cubic inch. The typical ratio of the volume of the anterior cavity to the volume of the posterior cavity is about 1:5.

There are a pair of connector tubes 102 and 104, respectively, extending from the openings 106 and 108 in opposed ends 112d and 112e of the shell 112 which are aligned along the central longitudinal axis X of the device 100. These connector tubes 102 and 104 have barbed ends 102a and 104a, respectively, that assist in holding these connector tubes firmly in feeding tubes 109a and 109b connected to the patient in the conventional manner. Preferably, the connector tubes 102 and 104 are made of polymethyl methacrylate (PMMA) and glued in position using an adhesive to the feeding tubes 109a and 109b.

The partition wall 118 has a central opening 120 aligned with the central longitudinal axis X of the device 100. Seated within this opening 120 is a connector tube 122 which is in axial alignment with the connector tubes 102 and 104 along the central longitudinal axis X of the device 100. This tube 122 is made of silconized rubber and it has one open end 122a in communication with the posterior cavity 116, and another open end 122b in communication with a chamber 124a of a one-way valve 124 seated on the floor 112a of the shell 112. At a predetermined pressure the fluid entering the valve 124 exits the valve through a slit-like opening 124b (FIG. 3) opposite the tube 122. Thus, fluid from the cranial cavity of a patient can flow from the feeding tube 109a that is connected to the connector tube 102, through this connector tube 102 into the posterior cavity 116, then through the tube 122 into the chamber 124a in the valve 124, and then out the slit-like opening 124b into the posterior cavity 116, and then out this posterior cavity through the connector tube 104 and the other feeding tube 109 connected to the body of the patient, usually to the stomach or heart.

The size of the device 100 is critical. In the illustrated embodiment, its total volume does not exceed about 0.12 cubic inch. It has a height of about 0.23 inch. It has a width which is 0.632 inch. It has a length of about 0.88 inch (excluding the connector tubes 102 and 104). As shown in FIG. 1, both the anterior end 112d and the posterior end 112e are tapered to a relativity pointed end section from which the connector tubes 102 and 104 project outwardly. Because of the unique aerofoil-like shape of the device 100, it is easy for the physician to insert the device in to an incision made, for example, behind the ear of an infant patient, stretching the patient's skin to cover the device 100, allowing the pointed end section with the device's smooth domed roof 112a to slip into the incision with minimal effort.

The device 100 is designed to alleviate blockages in either the anterior or posterior ends 112d and 112e. In the anterior end 112d, if there is a blockage between the connector tube 102 and the patient's brain, the physician, using a syringe (not shown) with a needle on its end, injects a normal saline solution into the anterior cavity 114 by piercing the patient's skin and the roof 112a of the shell 112 with the needle, forcing the saline solution into the anterior cavity 114. This forces fluid in the anterior cavity 114 to flow out the connector 102 into the feeding tube 109a to flush the feeding tube. The posterior cavity 116, which is filled with fluid from the patient's brain, is compressed when there is a blockage at the posterior feeding tube 109b. The physician merely presses on the exterior of the patient's skin to depress the roof 112a, reducing the volume of the posterior cavity 116 to force fluid out the connector tube 104 into the feeding tube 109b.

The device 100 is manufactured using insert molding techniques. First the components of the valve 124 are assembled, and then the valve and the connector tubes 102, 104 and 122 are placed in an insert mold (not shown). Next, the material for the shell 112 is injected in a molten state into the mold to form on solidifying the roof 112a, floor 112b, and partition wall 118 of the shell 112. When the molten material solidifies, the valve and connector tubes are held firmly in position.

The Valve

The valve 124 is of the type illustrated in U.S. Pat. No. 5,411,473, but it is designed to handle approximately 300 times higher flow rates than the Glaucoma Valve, or approximately 0.3 milliliters per minute. The components of this valve 124 as illustrated in FIGS. 4 through 8 are assembled and glued together as discussed in U.S. Pat. No. 5,411,473. These components includes a rectangular bottom plate 1, a rectangular, flexible, siliconized rubber membrane 2, and a rectangular top plate 3. The membrane 2 is originally in a non-folded condition as shown in FIG. 8. It has a length of about 0.530 inch and a width of about 0.310 inch and a thickness in excess of about 0.0075 inch, typically about 0.01 inch. The membrane is folded in half along a center line C. The length of the folded membrane is substantially the same as the length of the bottom and top plates I and 3, and these plates have about the same dimensions. There is an aperture in the membrane 2 along this center line C in which the connector tube 122 is inserted. A medical grade, biocompatible adhesive is used to bond the tube 122 to the aperture 5 of the membrane 2. The tube 122 is connected to the membranes prior to placing the assembly of the tube and valve in the insert mold.

To assemble the valve 124, the membrane 2 is first folded so that overlapping edges 4 (FIG. 3) of the folded membrane 2 create between the two halves of the membrane 2 the internal chamber 124a upon assembly of the valve and the slit-like opening 124b at the end of this chamber. The chamber 124a has trapezoidal configuration. In response to a predetermined pressure within the chamber 124a, fluid will then pass through the slit-like opening 124b. Tension is applied to the overlapping edges 4 to maintain the slit 6 in a normally closed state. This enables the valve 124 to function as a one-way directional flow device. To create this tension, the folded membrane 2 is stretched and placed between the top plate 3 and the bottom plate 1 to hold the stretched membrane in tension. Next, the folded membrane 2 is placed between precisely aligned and spaced apart top plate 3 and a bottom plate 1. These plates 1 and 3, with the membrane 2 stretched and sandwiched between them, are pressed together and interlocked by pins 39 in the bottom plate 1 which pass through aligned holes 40 in the membrane and bores 41 in the top plate 3. Grooves 44 in the bottom plate 1 and fingers 45 in the top plate 3 interlock and clamp the folded membrane 2 firmly between the top plate 3 and the bottom plate 1. Ultrasonic welding is used to bond the bottom plate 1 and the top plate 3 together. The valve 124 is assembled with the connector tube 122 affixed to the membrane 2. The assembly of membrane and plates is able to withstand internal pressure in the chamber 124a in excess of 60 millimeters of mercury (Hg).

SCOPE OF THE INVENTION

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiment disclosed. On the contrary, the intention is to cover all modifications and alternate constructions coming within the spirit and scope of the invention as generally expressed by the following claims, which particularly point out and distinctly claim the subject matter of the invention.

What is claimed is:

1. A medical device for draining fluid and having a central longitudinal axis including a shell made of a flexible, resilient material and including an anterior cavity and a posterior cavity separated by a partition wall, said partition wall having an opening therein aligned with the central longitudinal axis said shell having opposed ends that are tapered and a maximum height which is 0.35 inch, a maximum width which is 0.65 inch, and a maximum length which is 1.2 inch, the anterior cavity having a volumetric capacity ranging between 0.018 and 0.030 cubic inch and the posterior cavity having a volumetric capacity ranging between 0.100 and 0.150 cubic inch, and the shell having maximum volume of 0.275 cubic inch, an inlet tube having a first end adapted to be placed in communication with a fluid and a second end in communication with anterior cavity and an outlet tube having a first end in communication the posterior cavity and a second end adapted to allow fluid to drain therefrom, a one-way directional flow valve housed within the posterior cavity and connected to the partition wall, said one-way directional flow valve having a pair of overlying membranes in tension which provide a chamber with a slit-like opening adapted to allow fluid to exit the one-way directional flow valve and flow into the posterior cavity, said overlying membranes being form from a single sheet of material which is folded to form the slit-like opening, said one-way directional flow valve having an inlet end which is in communication with the anterior cavity through the opening in the partition wall and an outlet end in communication with the posterior cavity.

2. The medical device of claim 1 where the flexible, resilient shell material is self sealing to allow the shell to be pierced with a needle which upon withdrawal leaves a puncture which is sealed due the resiliency of the material.

3. The medical device of claim 2 where the flexible, resilient shell material is siliconized rubber.

4. The medical device of claim 1 where the anterior cavity has a maximum volumetric capacity of 0.030 cubic inch and the posterior cavity has a maximum volumetric capacity of 0.110 cubic inch.

5. The medical device of claim 1 where the shell has an aerofoil-like shape and a height ranging between 0.20 and 0.35 inch, a width ranging between 0.55 and 0.85 inch, and a length ranging between 0.8 and 1.2 inch.

6. The medical device of claim 1 where the single sheet is a siliconized rubber material, and a pair of plates maintain the membrane in tension.

7. The medical device of claim 6 where the sheet of siliconized rubber material has a thickness of at least 0.0075 inch.

8. The medical device of claim 7 where the folded sheet of siliconized rubber material and the pair of plates have a substantially rectangular configuration.

9. The medical device of claim 1 where the one-way directional flow valve has a height ranging between 0.100 and 0.175 inch, a width ranging between 0.60 and 0.80 inch, and a length ranging between 0.35 and 0.65 inch.

10. The medical device of claim 1 where the chamber of the one-way directional flow valve has a trapezoidal configuration with a minimum volumetric capacity of 0.03 cubic inch to a maximum volumetric capacity of 0.05 cubic inch.

11. The medical device of claim 1 manufactured by insert molding where the inlet tube, the outlet tube, and the one-way directional flow valve are placed in with a mold which is then filled with material to form the shell.

12. The medical device of claim 1 where the shell is adapted to expand or contract in response to pressure.

13. A method for treating hydrocephalus by draining the fluid from the cranial vault of a patient, including the steps of
  (a) providing a medical device including
    a shell including anterior and posterior cavities, said shell having opposed tapered ends and a maximum height which is 0.35 inch, a maximum width which is 0.65 inch, and a maximum length which is 1.2 inch, the anterior cavity having a volumetric capacity ranging between 0.018 and 0.030 cubic inch and the posterior cavity having a volumetric capacity ranging between 0.100 and 0.150 cubic inch, and the shell having maximum volume of 0.275 cubic inch,
    a pair of tubes, each tube having free ends and one tube in communication with one cavity and the other tube in communication with the other cavity, and
    a one-way directional flow valve housed within the one cavity that at a predetermined pressure allows fluid to flow through one tube into one cavity and then through the one-way directional flow valve into the other cavity and finally exiting the device through the other tube, said one-way directional flow valve having a pair of overlying membranes in tension which provide a chamber with a slit-like opening adapted to allow fluid to exit the one-way directional flow valve and flow into the posterior cavity, said overlying membranes being form from a single sheet of material which is folded to form the slit-like opening,
  (b) attaching the medical device to the patient,
  (c) inserting a free end of one tube into the cranial vault to enable fluid to drain through the free end of the one tube into the one cavity in the medical device,
  (d) inserting a free end of the other tube into the patient's body to enable fluid to drain from the other cavity into the body of the patient.

14. A medical device having a central longitudinal axis, and including
  a shell made of a flexible, resilient material and including an anterior cavity and a posterior cavity separated by a partition wall, said partition wall having an opening therein aligned with the central longitudinal axis,
  said shell having an aerofoil-like shape with opposed ends that are tapered and a maximum height which is 0.35 inch, a maximum width which is 0.65 inch, and a maximum length which is 1.2 inch,
  said anterior cavity having a volumetric capacity ranging between 0.018 and 0.030 cubic inch and said posterior cavity having a volumetric capacity ranging between 0.100 and 0.150 cubic inch, and said shell having a maximum volume of 0.275 cubic inch,
  an inlet tube having a first end adapted to be placed in communication with a fluid and a second end aligned with the central longitudinal axis and in communication with anterior cavity and an outlet tube having a first end aligned with the central longitudinal axis and in communication the posterior cavity and a second end adapted to allow a fluid to drain therefrom, and
  a one-way directional flow valve connected to the partition wall and housed within the posterior cavity to least partially extend into the posterior cavity,
  said one-way directional flow valve including an inlet end aligned with the opening in the partition wall and in communication with the anterior cavity through said opening in the partition wall and an outlet end in communication with the posterior cavity and adapted to allow fluid to exit the one-way directional flow valve and flow into the posterior cavity.

15. A method for treating hydrocephalus by draining the fluid from the cranial vault of a patient, including the steps of
  (a) inserting into an incision in the patient with minimal effort a medical device having a central longitudinal axis, and including
    a shell made of a flexible, resilient material and having an aerofoil-like shape with opposed ends that are tapered and an anterior cavity and a posterior cavity,
    said shell having a maximum height which is 0.35 inch, a maximum width which is 0.65 inch, and a maximum length which is 1.2 inch,
    said anterior cavity having a volumetric capacity ranging between 0.018 and 0.030 cubic inch and said posterior cavity having a volumetric capacity ranging between 0.100 and 0.150 cubic inch, and said shell having a maximum volume of 0.275 cubic inch,
    an inlet tube having a first end adapted to be placed in communication with the fluid and a second end in communication with anterior cavity and an outlet tube having a first end in communication the posterior cavity and a second end adapted to allow the fluid to drain therefrom, and
    a one-way directional flow valve connected to the partition wall housed within the posterior cavity to least partially extend into the posterior cavity,
    said one-way directional flow valve including an inlet end in communication with the anterior cavity through the opening in the partition wall and an outlet end in communication with the posterior cavity and adapted to allow the fluid to exit the one-way directional flow valve and flow into the posterior cavity,
  (b) inserting a free end of the one tube into the cranial vault to enable the fluid to drain through the free end of the one tube into the anterior cavity in the medical device,
  (c) inserting a free end of the other tube into the patient's body to enable fluid to drain from the posterior cavity into the body of the patient, (d) when a blockage occurs upstream of the valve, piercing the shell with the needle of a syringe to inject into the anterior cavity liquid to force said liquid into the anterior cavity, said shell self sealing upon withdrawal of the needle due the resiliency of the material, and (e) when a blockage occurs downstream of the valve, applying pressure to the posterior cavity through the patient's skin.

* * * * *